US005760216A

United States Patent [19]
Chorghade et al.

[11] Patent Number: 5,760,216
[45] Date of Patent: Jun. 2, 1998

[54] USE OF SYNTHETIC METALLOPORPHYRINS FOR PREPARATION AND PREDICTION OF DRUG METABOLITES

[75] Inventors: Mukund S. Chorghade, Gurnee, Ill.; David H. Dolphin, Vancouver, Canada; David R. Hill, Gurnee, Ill.; Fumio Hino, Tokyo, Japan; Elaine C. Lee, Wheeling, Ill.

[73] Assignee: Abbott Laboratories, Abbott Park, Ill.

[21] Appl. No.: 520,842

[22] Filed: Sep. 12, 1995

Related U.S. Application Data

[63] Continuation of Ser. No. 306,801, Sep. 15, 1994, abandoned.
[51] Int. Cl.$^6$ .......................... C07B 47/00; C07C 29/48; C07D 301/03
[52] U.S. Cl. .......................... 540/145; 424/9.2; 514/410; 534/10; 534/14
[58] Field of Search .......................... 424/9.2, 9.362; 534/10, 14; 540/138, 145, 474, 472; 514/410

[56] References Cited

FOREIGN PATENT DOCUMENTS

| 0636628 | 2/1995 | European Pat. Off. . |
| 8807988 | 10/1988 | WIPO . |

OTHER PUBLICATIONS

Shelnutt, J.A., et al., "Photochemically–driven Biomimetic Oxidation of Alkanes and Olefins", *Tetrahedron Lett.*, 30(39):5231–5234 (1989).

Mansuy, D., et al., "Biomimetic Oxidation of Hydrocarbons and Drugs by Metalloporphyrinic Systems", *Bull. Soc. Belg.*, 94(11):959–965 (1986).

Gaggero, N., et al., "Oxidation of SR 48117, an antagonists of vasopressin V1a receptors, by biomimetic catalysts based on metalloporphyrin or Schiff–base complexes", *Bull. Soc. Chim. Fr.*, 131(6):706–712 (1994).

Carrier, M.N., et al., "Studying drug metabolic oxidation with biomimetic metalloporphyrin systems: Problems and solutions in the case of lidocaine", *Bull. Soc. Chim. Fr.*, 130(3):405–416 (1993).

Vidal, M., et al., "Model Systems for Oxidative Drug Metabolism Studies: Catalytic Behaviour of Water–Soluble Metalloporphyrins Depends on Both the Intrinsic Robustness of the Catalyst and the Nature of the Substrates", *Drug Met. Dispos.*, 21(5):811–817 (1993).

Bernadou, J., et al., "Model Systems for Metabolism Studies: Biomimetic Oxidation of Acetaminophen and Ellipticine Derivatives with Water–Soluble Metalloporphyrins Associated to Potassium Monopersulfate", *Drug Met. Disp.*, 19(2):360–365 (1991).

Sakurai, H., et al., "A Model System for Drug Metabolism in Isolated Hepatocytes; Oxidation of Cyclohexene by Metalloporphyrin Complexes", *J. Mol. Catal.*, 20(2):153–156 (1985).

*Primary Examiner*—Gary E. Hollinden
*Assistant Examiner*—Michael G. Hartley
*Attorney, Agent, or Firm*—Richard A. Elder; Michael J. Ward

[57] ABSTRACT

A method for the systematic and efficient synthetic preparation and identification of metabolites of a pharmaceutical product in order to study possible toxic and/or otherwise biologically-active metabolites of such pharmaceutical products as early and conveniently as possible in the very expensive drug development process, comprising adding samples of the pharmaceutical product to a series of combinations of a synthetic metalloporphyrin (SMP) with a synthetic metalloporphyrin-co-oxidizing reagent in the presence of a suitable solvent, under specified conditions, in a manner such that each sample of pharmaceutical product is reacted with a different combination of synthetic metalloporphyrin, SMP-co-oxidizing reagent and solvent, followed by separation and isolation of the resulting oxidative products, then confirmation of the identity of metabolites from the pre-identified oxidative products by appropriate animal model studies, and subjecting the actual metabolites prepared in larger quantities by the above method to toxicologic, pathologic, histopathologic, mechanistic or genotoxic testing in order to identify toxic and/or otherwise metabolically-active beneficial or detrimental individual metabolites.

7 Claims, No Drawings

USE OF SYNTHETIC METALLOPORPHYRINS FOR PREPARATION AND PREDICTION OF DRUG METABOLITES

This application is a continuation of U.S. Ser. No. 08/306.801 filed Sep. 15, 1994, now abandoned, the benefit of which is claimed under 35 USC 120.

TECHNICAL FIELD

Synthetic metalloporphyrin (SMP) compounds serve as models of oxidative catalysts in biological systems. Oxidative products of pharmaceutical compounds, which products are useful in the prediction of biological metabolites, may be systematically and efficiently prepared by reacting the pharmaceutical compounds with specified combinations of synthetic metalloporphyrin catalysts, SMP-co-oxidizing reagents and solvents, followed by separation and identification of such oxidative products, which oxidative products may then be subjected to toxicologic, pathologic, histopathologic, mechanistic or genotoxic testing for determining the toxicity and other biological properties of the metabolites of the original pharmaceutical compounds.

BACKGROUND OF THE INVENTION

In humans and other animals most drugs are metabolized in the liver. Many drug metabolites are formed by oxidative mechanisms catalyzed primarily by heme- and cytochrome-containing enzymes. Of these, the cytochrome P450-dependent monooxygenases provide the primary catalysis in most biological oxidations (cf., *Cytochrome P-450: Structure, Mechanism and Biochemistry*, P. R. Ortiz de Montellano, ed., Plenum Press, N.Y., 1986).

The metabolic process which a drug compound undergoes in the body contibutes in large measure to the efficacy of the compound for a particular purpose (sometimes actually resulting in creation of the active compound itself), to whatever side-effects a compound may possess, and to the presence or absence of toxicity or undesirable biological activity of its metabolites. These factors are major contributors to the success or failure of a particular pharmaceutical compound and the importance of the metabolic process has been sufficient to justify the vast amounts of research effort which has been expended in the past thirty years in studying the mechanisms of the oxidative metabolic processes.

Pharmacologists, being aware of the importance of drug metabolites to the future of pharmaceutical product candidates, have been involved in the attempts to identify and isolate such compounds. They have traditionally tried to obtain sufficient quatities of these metabolites as early as possible in the very expensive drug development process, in order to conduct further toxicological and pharmacological studies on them.

Several problems are associated with the use of biological systems in studying drug metabolism, however. In particular, both animal and in vitro metabolic studies produce very small amounts of metabolites, thus making identification of these metabolites difficult. These metabolites generally must be isolated in order to be identified, and pharmacologists do not know in advance for which potential metabolites they should be looking. Also, animal studies are notoriously expensive to conduct, since large numbers of animals are required for these metabolic studies, and even when identified, the metabolites may not be easily or efficiently synthesized for purposes of further testing, especially when larger amounts of metabolites are required for such testing.

Recently, investigators have begun to study model systems of the biological oxidations in which synthetic metalloporphyrins are utilized as mimics of the cytochrome P450-dependent monooxygenase catalysts. A limited number of reviews of the literature in this new field have been published, including those by Xie and Dolphin ("Biological Oxidations with Heme Proteins," in *Metalloporphyrins Catalyzed Oxidations*, F. Montanari and L. Casella, eds., Kluwer Academic Publishers, The Netherlands, 1994, pp 269–306); and Montanari et al. (*Rev. Heteroat. Chem.*, 6:94–141 (1992)).

The first SMPs studied were found to be unstable, but improvements in molecular stability and increases in the turnover of catalytic reactions have been obtained with the introduction of additional atoms into the synthetic metalloporphyrin molecules. The work of Dolphin and others has shown that addition of halogen atoms onto the aryl groups and the β-pyrrolic positions of meso-tetraarylporphyrins makes intermediate oxo-porphyrin complexes more electron deficient and more sterically protected and thus provides for more effective oxidation catalysis (see, for example, Xie and Dolphin, op. cit.).

However, model studies with these halogenated synthetic metalloporphyrins have been hampered by lack of convenient access to these catalytic compounds themselves. As these catalysts are not commercially available, they must generally be prepared in the researcher's laboratories. For examples of methods currently used for synthesis of synthetic metalloporphyrins, representative procedures are given by Dolphin et aL, U.S. Pat. No. 4,892,941, issued Jan. 9, 1990; Traylor et al., *Inorg. Chem.*, 26:1338–1339 (1987); Rocha Gonsalves et al., *Tetrahedron Lett.*, 32:1355–1358 (1991); Hoffmann et al., *Tetrahedron Lett.*, 31:1991–1994 (1990); and Wijesekera et al., *Angew. Chem., Int. Ed. Engl.*, 29:1028–1030 (1990).

To date, few other uses of synthetic metalloporphyrins for the study of the oxidative metabolism of drugs have been reported, however. Carrier et al. (*Bull. Soc. Chim. Fr.*, 130:405–416 (1993)), who studied lidocaine oxidation with various cytochrome P450 model systems and produced thereby some of the known primary metabolites of lidocaine, have suggested that reaction conditions and the metalloporphyrins themselves might be varied to give differing amounts of oxidation products, or in some cases, different products entirely. (In contrast, by applying the novel method of the present invention, the remaining known metabolites, as well as some additional oxidation products which are being considered as possible additional metabolites in ongoing studies, have been produced.)

Matsumoto et al. (*Drug. Metab. Disp.*, 19:768–780 (1991)), in a very narrow study, examined the oxidation of piperidine ring systems by cytochrome P450 model metalloporphyrins. Also, novel oxidation products of erythromycin, which are not, however, biological metabolites of that compound, have been prepared by D. R. Hill et al. (*Tetrahedron Letters*, manuscript in preparation).

It was therefore an objective of this invention to provide pharmacologists with a method of systematically and efficiently producing and identifying the metabolites of drug candidates to permit them to determine whether these metabolites possess any unacceptable toxicity profiles and/ or if they have either desirable or undesirable biological activity as early as possible in the expensive drug development process. It was also an objective of this invention to provide a method of producing and identifying oxidative products of a pharmaceutical candidate from which the metabolites of a pharmaceutical product could be identified before animal or biological studies are done.

It was another objective of this invention to provide a synthetic method of producing quantities of oxidation products of drug candidates, which products may have been identified as metabolites by biological testing, in quantities sufficient to allow for toxicological and futher biological tests thereon, at an early stage in the discovery process. It was a further objective of this invention to provide acceptable ways of reducing the amount of animal testing required in the development of a drug candidate.

SUMMARY OF THE INVENTION

The present application describes a method for the systematic and efficient synthetic preparation and identification of metabolites of a pharmaceutical product in order to study possible toxic and/or otherwise biologically-active metabolites of such pharmaceutical products as early and conveniently as possible in the very expensive drug development process, comprising adding samples of the pharmaceutical product to a series of combinations of a synthetic metalloporphyrin (SMP) with a synthetic metalloporphyrin-co-oxidizing reagent in the presence of a suitable solvent, under specified conditions, in a manner such that each sample of pharmaceutical product is reacted with a different combination of synthetic metalloporphyrin, SMP-co-oxidizing reagent and solvent, followed by separation and isolation of the resulting oxidative products, then confirmation of the identity of metabolites from the pre-identified oxidative products by appropriate animal model studies, and subjecting the actual metabolites prepared in larger quantities by the above method to toxicologic, pathologic, histopathologic, mechanistic or genotoxic testing in order to identify toxic and/or otherwise metabolically-active beneficial or detrimental individual metabolites.

DETAILED DESCRIPTION OF THE INVENTION

The present invention is directed to a process for the systematic preparation of oxidative products of a drug candidate compound, comprising reacting the drug candidate compound with a series of combinations of a member of group of synthetic metalloporphyrins, as defined below, with a member of a group of SMP-co-oxidizing reagents, as defined below, in the presence of a suitable solvent, such as, for example, methylene chloride, acetonitrile, acetonitrile/water, methanol/water, buffered aqueous solutions thereof, or the like, for a period of up to twenty-four (24) hours, at a temperature from 0° C. to reflux temperature of the solvent, in a manner such that each sample of drug compound is reacted with a different combination of synthetic metalloporphyrin, SMP-co-oxidizing reagent and solvent, followed by separating and isolating each resulting oxidative product by gas, liquid/liquid, or solid/liquid chromatography, HPLC, or the like. Said oxidative products may then be identified by analytical means such as, for example, NMR, MS, IR, or UV spectroscopy, or the like.

These oxidative products are then identified to a pharmacologist who uses them as predictors to identify actual metabolites of the original drug candidate compound in studies with appropriate animal models. And the actual metabolites are then subjected (in larger quantities prepared by methods according to the above process which has been optimized to prepare these specific metabolites) to various biological tests in order to identify toxicity and/or other desirable or undesirable biological activity of these metabolites as early as possible in the very expensive drug development process.

The term "synthetic metalloporphyrin," as used herein, refers to porphyrin compounds having the structures:

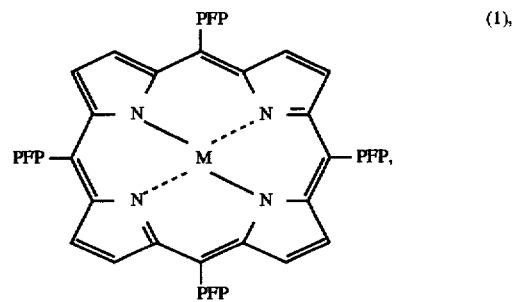

(1), wherein PFP represents perfluorophenyl and M is selected from the group consisting of iron, manganese, chromium, ruthenium, cobalt, copper and nickel;

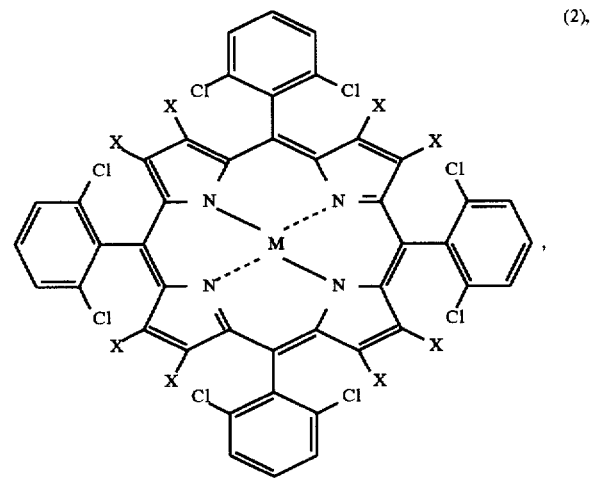

(2), wherein X is Cl, Br, $NO_2$, CN or sulfonate, and M is as described above; or

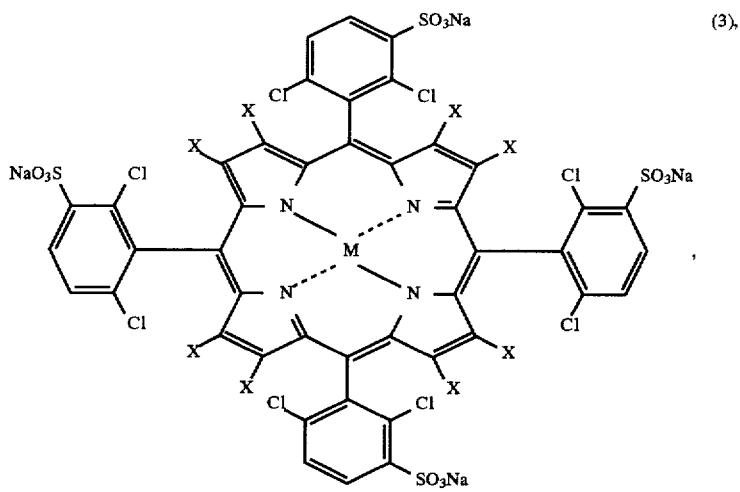

(3), wherein X and M are as described above.

The abbreviations for the synthetic metalloporphyrins used herein include: perfluorotetraphenyl Fe(III) porphyrin for the compound of formula (1) above, wherein M is iron; perfluorotetraphenyl Mn(II) porphyrin for the compound of formula (1) above, wherein M is manganese; octachloro-octabromo Fe(III) porphyrin for the compound of formula (2) above, wherein X is Br and M is iron; octachloro-octabromo Mn(II) porphyrin for the compound of formula (2) above, wherein X is Br and M is manganese; octachloro-octachloro Fe(III) porphyrin for the compound of formula (2) above, wherein X is Cl and M is iron; octachloro-octachloro Mn(II) porphyrin for the compound of formula (2) above, wherein X is Cl and M is manganese; octachloro-octabromo tetrasulfonato Fe(III) porphyrin for the compound of formula (3) above, wherein X is Br and M is iron; octachloro-octabromo tetrasulfonato Mn(II) porphyrin for the compound of formula (3) above, wherein X is Br and M is manganese; octachloro-octachloro tetrasulfonato Fe(III) porphyrin for the compound of formula (2) above, wherein X is Cl and M is iron; and octachloro-octachloro tetrasulfonato Mn(II) porphyrin for the compound of formula (2) above, wherein X is Cl and M is manganese.

Other synthetic metalloporphyrins suitable for use herein may have effective catalytic activity as a result of substitution with electron-withrawing and sterically-protecting groups, such as, for example, substitution of nitro, cyano or sulfonate for the chlorine atoms on the phenyl rings and/or the porphyrin rings of compounds of formulas (2) or (3) above, or carboxyl substitution for the sulfonato groups of compounds of formulas (2) or (3) above. In general, these synthetic metalloporphyrins are highly reactive, are not rapidly destroyed under strong oxidizing conditions, and are capable of effecting catalytic oxidations with high turnover numbers.

The preferred synthetic metalloporphyrins envisioned for use in this invention are the compounds selected from the group of compounds comprising formulas (2) or (3) above.

The more preferred synthetic metalloporphyrins for use herein are the compounds of formulas (2) or (3) above wherein M is iron or manganese, and are selected from the group comprising octachloro-octabromo Fe(III) porphyrin, octachloro-octabromo Mn(II) porphyrin, octachloro-octachloro Fe(III) porphyrin, octachloro-octachloro Mn (II) porphyrin, octachloro-octabromo tetrasulfonato Fe(III) porphyrin, octachloro-octabromo tetrasulfonato Mn(II) porphyrin, octachloro-octachloro tetrasulfonato Fe(III) porphyrin, and octachloro-octachloro tetrasulfonato Mn(II) porphyrin.

The synthetic metalloporphyrins may be prepared by known methods (see the references cited in the Background, above) wherein a suitable zinc-containing metalloporphyrin, such as meso-tetrakis(2,6-dihalophenyl)-porphyrinato-zinc (II), wherein "halo" is chloro, bromo, fluoro, or indo, is reacted with one of several active halogenating agents, followed by removal and replacement of the zinc atom with the desired active metal ion. They may also be prepared by an improved method for the preparation of a porphyrin-ring halogenated synthetic metalloporphyrin, wherein the halogenating agent may be a free halogen, such as $Cl_2$ or $Br_2$, in a suitable polar solvent, such as methanol, ethanol, or the like, and the reaction may be performed at lower temperatures, thus resulting in enhanced yields of the desired product.

Such a synthetic metalloporphyrin may be more preferably prepared by reacting a suitable zinc-containing metalloporphyrin, such as meso-tetrakis(2,6-dichlorophenyl)-porphyrinato-zinc(II), for example, with a free halogen, such as $C_2$ or $Br_2$, in a suitable polar solvent, such as methanol, ethanol, or the like, at a temperature of from 0° C. to ambient, followed by removal and replacement of the zinc atom with the desired active metal ion.

The synthetic metalloporphyrins may be attached to support materials in adsorbed, covalently- or ionically-bonded manners, for example, adsorbed onto diatomaceous earth. Such adsorbed preparations may be utilized in the form of suspensions or in fixed format, such as, for example, in columns.

The term "SMP-co-oxidizing reagent," as used herein, refers to those oxidizing agents suitable for use with a synthetic metalloporphyrin, and include, for example, iodosobenzene, sodium hypochlorite, potassium monopersulfate, ozone, and peroxides, such as hydrogen peroxide, m-chloroperbenzoic acid, cumene hydroperoxide or tert-butyl hydroperoxide.

Preferred SMP-co-oxidizing reagents are those selected from the group comprising iodosobenzene, sodium hypochlorite, tert-butyl hydroperoxide and potassium monopersulfate.

The co-oxidizing reagent is preferably added to the reaction mixture gradually, in small quantities, with a fresh charge of oxidant being added after a period of 3 hours.

The solvent in which the above reactions are carried out may be any solvent known to those skilled in the art which does not interact unfavorably with the synthetic metalloporphyrin and/or the co-oxidizing reagent. The solvent may be selected to favor solubility of the drug compound or the synthetic metalloporphyrin, or for ease of recovery and purification of the product.

Preferred solvents are those selected from the group comprising $CH_2Cl_2$, $CH_3CN$, 20% methanol in $H_2O$, 20% $CH_3CN$ in $H_2O$, or aqueous solutions buffered to various pH levels.

In a preferred embodiment of this process, the synthetic metalloporphyrins are selected from the group comprising octachloro-octabromo Fe(III) porphyrin, octachloro-octabromo Mn(II) porphyrin, octachloro-octachloro tetrasulfonato Fe(III) porphyrin, and octachloro-octachloro tetrasulfonato Mn(II) porphyrin; the SMP-co-oxidizing reagents are selected from the group comprising iodosobenzene, sodium hypochlorite, tert-butyl hydroperoxide, and potassium monopersulfate; and the solvents are those selected from the group comprising $CH_2Cl_2$, 20% $CH_3CN$ in $H_2O$, and buffered aqueous solutions.

The combining and reacting of the pharmaceutical compound, the synthetic metalloporphyrins, SMP-co-oxidizing reagents and the solvents may be achieved either simultaneously or serially with or without appropriate automated means, including the use of robotic devices. A "kit" of metalloporphyrin reagents and oxidizers may also be prepared for convenient use of this novel process, and is considered to be within the scope of the invention.

It is intended that this invention include optimization of reaction conditions by easy, rapid and repetitive experimentation to identify the appropriate combination of solvent, metalloporphyrins, oxidant and reaction conditions that produces the maximum number and/or amount of metabolites or of one or more desired metabolites. This logically leads to a subsequent scaled-up optimal process by which large amounts of one or more desired metabolites may be produced.

"Appropriate animal models" for use in confirming that the oxidative products prepared by the process above are actually metabolites of the pharmaceutical product being studied include those identified by methods well-known to pharmacologists for determining animal species which have metabolic processes for the particular product category which are similar to those of humans.

The process of the invention may be used in combination with an examination of the oxidative products produced thereby in toxicity tests, such as for example, acute, subchronic, or chronic studies involving clinical pathologic, histopathologic, mechanistic or genotoxicity protocols, or in other screens or protocols in use for determining biological activity, for identifying toxic or metabolically-active metabolites of a drug candidate.

SCHEMES

The oxidation products of the reactions herein are illustrated in the following schemes. Scheme 1 illustrates aminopyrine and its oxidation products. Scheme 2 shows the oxidation of 4-acetylaminoantipyrine (AP-10). Scheme 3 illustrates the oxidation product of 3-hydroxymethylaminopyrine (AP-5). Scheme 4 shows lidocaine and its oxidation products. Scheme 5 illustrates dimethylaniline and its oxidation products. Scheme 6 diagrams the preparation of octachloro-octahalo Zn(II) porphyrins, wherein the octachloroporphyrin on the left is reacted with molecular chlorine or bromine in methanol to give the octachloro-octahalo-porphyrin on the right. Scheme 7 shows the oxidation products of ABT-418. Scheme 8 shows the oxidation products of odapipam.

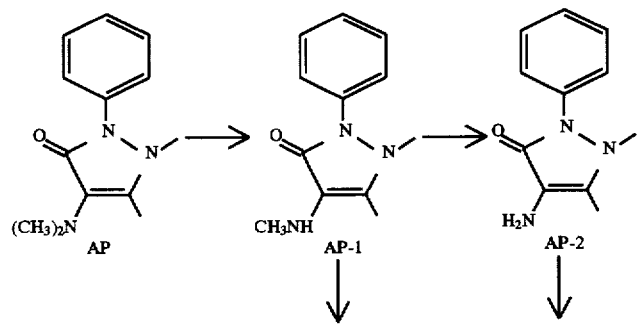

Scheme 1

-continued
Scheme 1
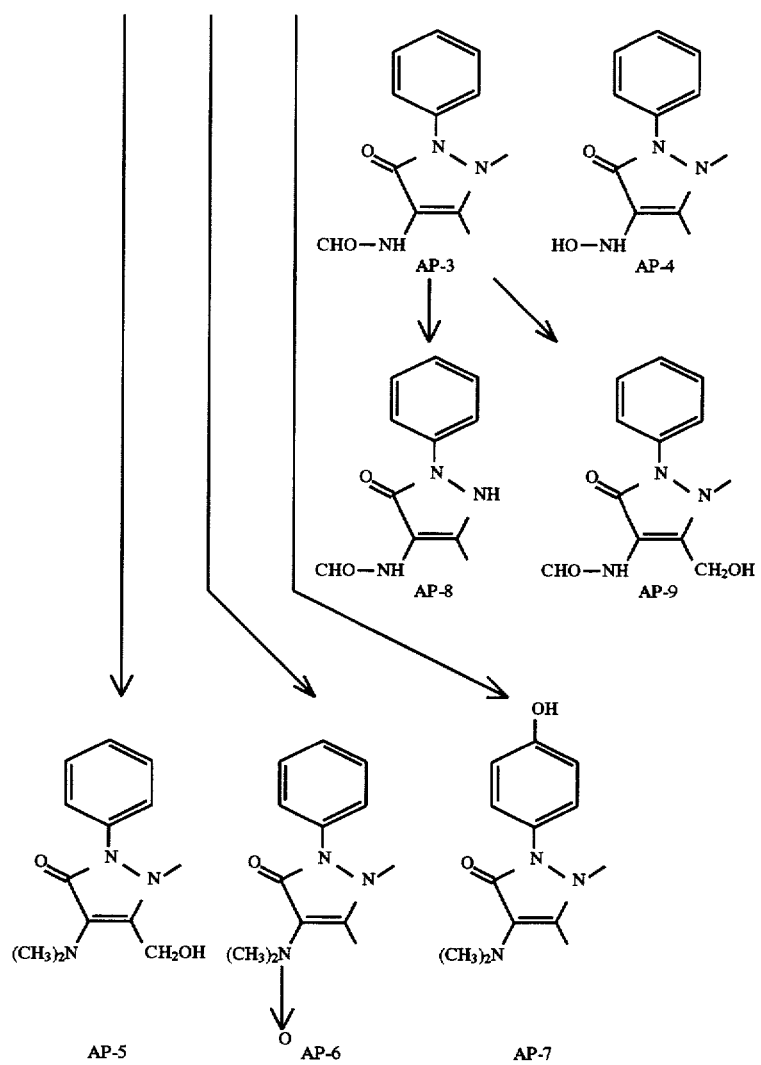
Scheme 2
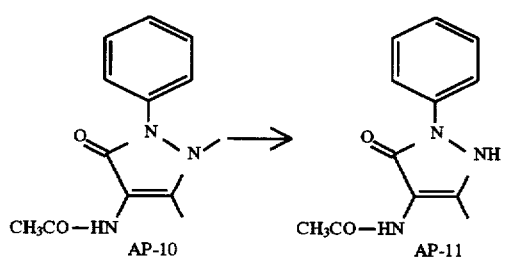
Scheme 3
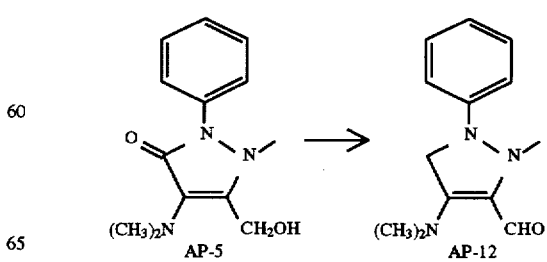

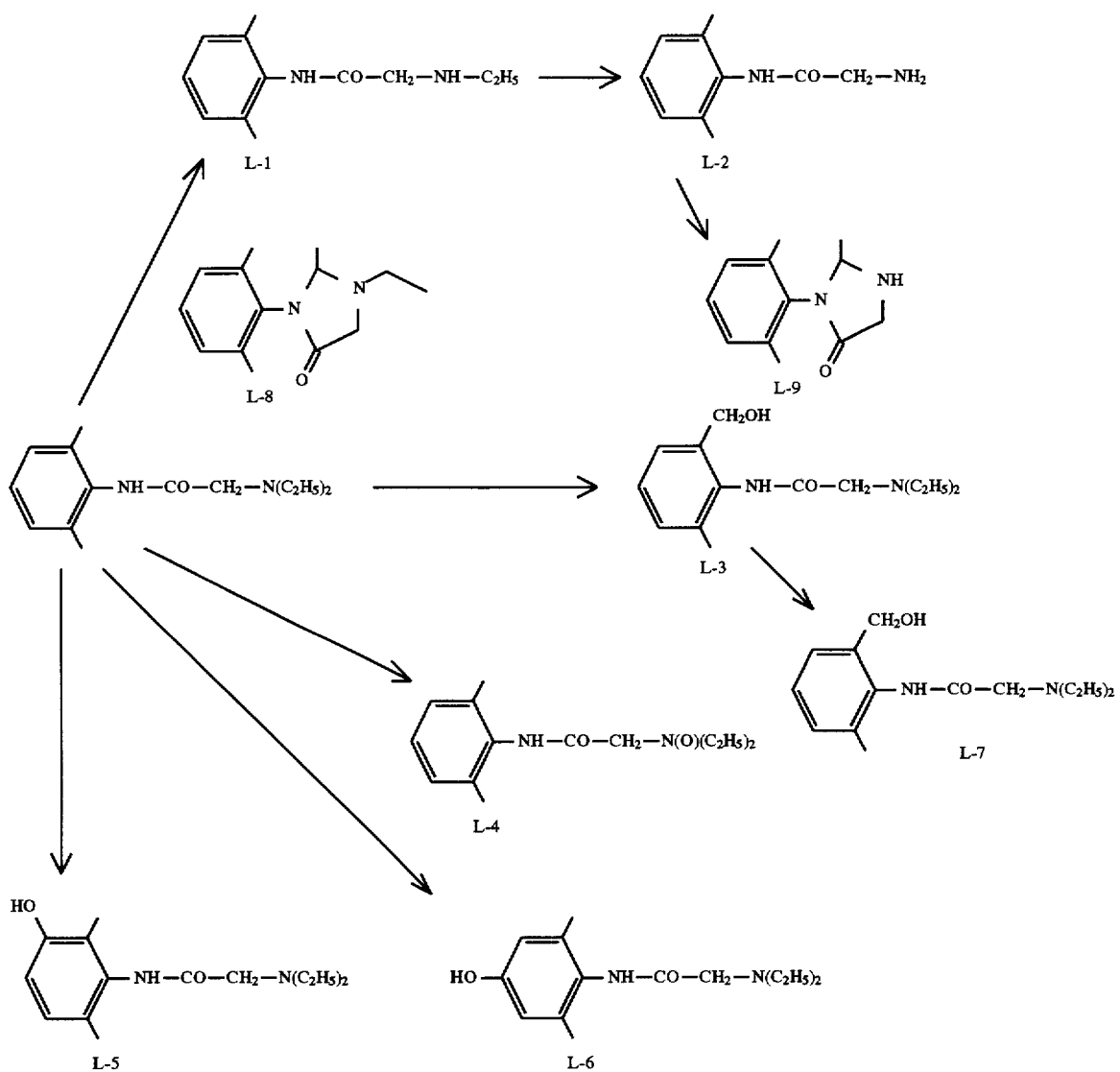
Scheme 4
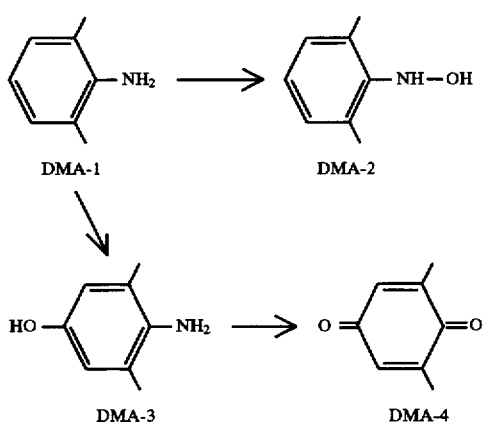
Scheme 5

Scheme 6

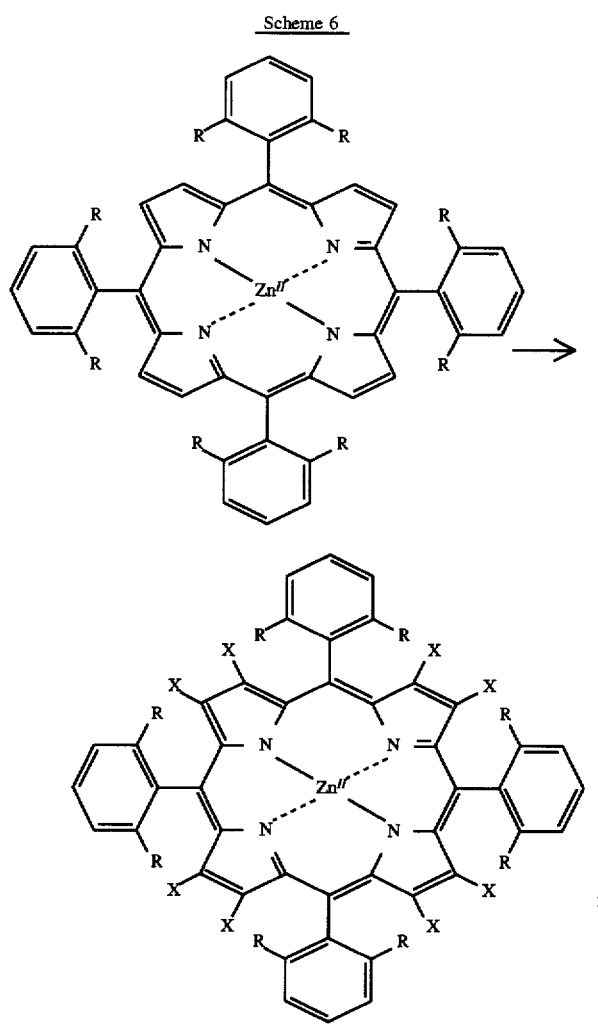

Scheme 7

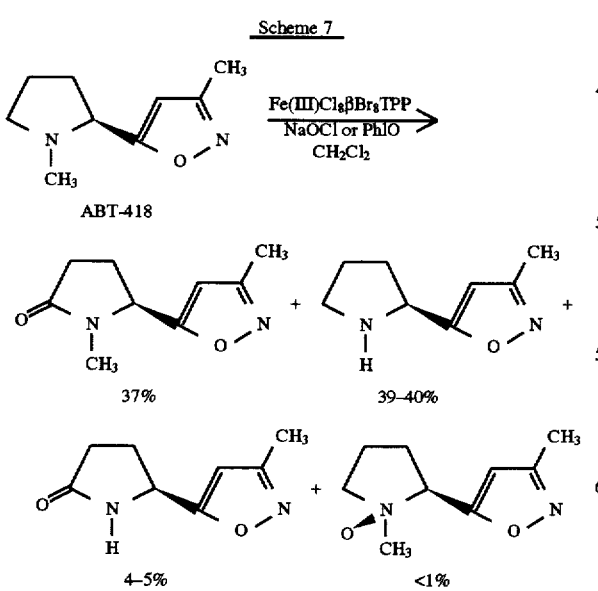

Scheme 8

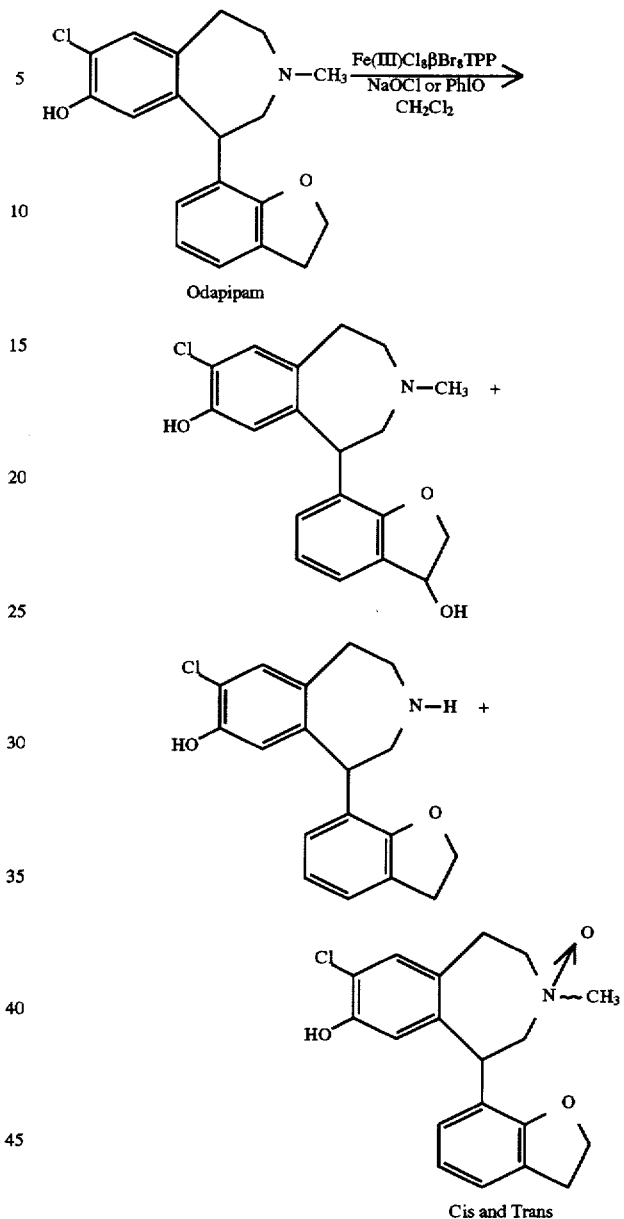

The following examples illustrate particular embodiments of the invention, and are not intended as a limitation upon the scope thereof.

EXAMPLE 1

Aminopyrine Metabolites

Aminopyrine hydrochloride was prepared from the free base (Aldrich) by treatment with HCl in ether. Iodosobenzene (1650 mg, 7.5 mmol, prepared according to the method of Saltzman et al., *Org. Synth.*, 43:60–61 (1963)) was added with stirring at room temperature in portions every 30 min to a solution of octachloro-octachloro tetrasulfonato Fe(III) porphyrin (6.2 mg 3.9 μmol) in 50 ml of 80:20 $H_2O:CH_3CN$ containing 678 mg (3.0 mmol) of aminopyrine. Two hr after the last addition of the oxidant, the solution was evaporated under reduced pressure at 50° C. The residue was dissolved in 20 ml of aqueous $Na_2CO_3$ solution, and the solution was extracted with $CH_2Cl_2$ (3×50 ml). The organic layer was dried over $Na_2CO_3$ and evaporated under reduced pressure. The residue was chromatographed on silica gel, eluting with 1:25 methanol:methylene chloride. Seven oxidation products were obtained from the eluate (see Scheme 2): 2,3-dimethyl-4-monomethylamino-1-phenyl-3-pyrazolin5-one (AP-1); 4-amino-2,3-dimethyl-1-phenyl-3-pyrazolin-5-one (AP-2); 4formylamino-2,3-dimethyl-1-phenyl-3-pyrazolin-5-one (AP-3); 2,3-dimethyl-4hydroxyamino-1-phenyl-3-pyrazolin-5-one (AP-4); 4-dimethylamino-3hydroxymethyl-2-methyl-1-phenyl-3-pyrazolin-5-one (AP-5); 4-dimethylamino-2,3-dimethyl-1-phenyl-3-pyrazolin-5-one-4-oxide (AP-6); and 4-dimethyl-2,3dimethyl-1-(4-hydroxyphenyl)-3-pyrazolin-5-one (AP-7), 4-formylamino-2-methyl1-phenyl-3-pyrazolin-5-one (AP-8), and 4-formylamino-3-hydroxymethyl-2methyl-1-phenyl-3-pyrazolin-5-one (AP-9).

The yields of these products were as shown in the column for Example 1 in Table 1 below. The AP-4, AP-7, AP-8 and AP-9 compounds are new metabolites, while the others are known metabolites of the oxidation of aminopyrine with liver microsomes or purified cytochrome P-450s.

TABLE 1

Yields of aminopyrine metabolites under varying reaction conditions

| | yields of metabolites (%) | | |
|---|---|---|---|
| metabolite | Example 1 | Example 2 | Example 3 |
| AP-1 | 4 | | |
| AP-2 | 53 | | |
| AP-3 | 17 | | |
| AP-4 | 2 | | |
| AP-5 | 2 | 78 | |
| AP-6 | 1 | | |
| AP-7 | 3 | | 16 |
| AP-8 | 1 | | |
| AP-9 | 1 | | |

EXAMPLE 2

Alternate Oxidation of Aminopyrine at pH 1

Iodosobenzene (66 mg, 0.3 mmol) was added with stirring at room temperature in portions over 30 min to a solution of octachloro-octachloro tetrasulfonato Fe(III) porphyrin (1 mg, 0.6 μmol) in 2 ml of 1:4 acetonitrile:pH 1 $H_2O$ (adjusted with 0.2N HCl) containing 28 mg (0.12 mmol) of aminopyrine. The solution was evaporated under reduced pressure. The residue was dissolved in satd aq. $Na_2CO_3$, and the products were extracted with 3×1 ml of methylene chloride. The organic layer was chromatographed over silica gel, eluting with methylene chloride. The solvent was evaporated under reduced pressure, and the residue was crystallized from methylene chloride:hexanes. Compound AP-5 was obtained as the major metabolite (22.7 mg, 78% yield), and was the only one identified quanitatively.

EXAMPLE 3

Alternate Oxidation of Aminopyrine in Organic Solvents

Aminopyrine hydrochloride was prepared from the free base (Aldrich) by treatment with HCl in ether. Iodosobenzene (66 mg, 0.3 mmol) was added with stirring at room temperature in portions over 30 min to a solution of octachloro-octachloro tetrasulfonato Fe(III) porphyrin (1 mg, 0.6 μmol) in 2 ml of 1:20 methanol:$CH_3CN$ containing 30 mg (0.13 mmol) of aminopyrine hydrochloride. The reaction was stirred for 10 min after the last portion of oxidant was added, and the solution was evaporated under reduced pressure. The residue was chromatographed over alumina, eluting with 5:1 methylene chloride:hexanes, and compound AP-7 was isolated in 16% yield.

EXAMPLE 4

Selective Oxidation of 4-amino-2,3-dimethyl-1-phenyl-3-pyrazolin-5-one (AP-2) to 2,3-dimethyl-4-hydroxyamino-1-phenyl-3-pyrazolin-5-one (AP-3)

4-Aminoantipyrine (0.12 mmol, Aldrich) and octachloro-octachloro tetrasulfonato Fe(III) porphyrin (0.6 μmol) were dissolved in 4 ml of pH 7 phosphate buffer and cooled to 0° C. To this was added iodosobenzene (66 mg, 0.3 mmol) was added in portions over 10 min. The reaction was stirred for 4 hr and extracted with 3×2 ml of methylene chloride and dried over $Na_2CO_3$. The organic layer was chromatographed over silica gel, eluting with methylene chloride, to yield 2,3-dimethyl-4-hydroxyamino-1-phenyl-3-pyrazolin-5-one (AP-3) in 30% yield.

EXAMPLE 5

Selective oxidation of 4-acetylaminoantipyrine (AP-8)

Cumene hydroperoxide (150 mg, 0.99 mmol) was added slowly to a solution of 4-acetylaminoantipyrine (120 mg, 0.49 mmol) and octachloro-octachloro tetrasulfonato Fe(III) porphyrin (15 mg, 0.95 μmol) held at 5° C., and the mixture was allowed to stand for 3 hr at room temperature. The mixture was made weakly basic with aqueous $Na_2CO_3$, and the product was extracted with 3×5 ml of methylene chloride. The organic extract was dried over $Na_2CO_3$ and evaporated under reduced pressure. The residue was chromatographed over basic alumina, eluting with 1:1 methylene chloride:hexane. The fraction containing the last band to come off the column was collected and evaporated under reduced pressure. The residue was crystallized from methylene chloride:hexane to obtain the compound AP-9 (see Scheme 3) in 32% yield.

EXAMPLE 6

Selective Oxidation of 3-hydroxymethylaminopyrine (AP-5)

Following the procedure of Example 2 above, 4-dimethylamino-3-hydroxymethyl-2-methyl-1-phenyl-3-pyrazolin-5-one (AP-5) was substituted for the aminopyrine thereof. After 2 hr of reaction at 5° C., the mixture was neutralized with 0.1N NaOH. The products were extracted with 3×5 ml of methylene chloride. The organic extract was dried over $Na_2CO_3$ and evaporated under reduced pressure. The residue was chromatographed over neutral alumina, eluting with methylene chloride, to obtain the 3-formyl derivative in 45% yield (AP-10, Scheme 4).

EXAMPLE 7

Oxidation of Lidocaine

Six mg (3.8 μmol) of octachloro-octachloro tetrasulfonato Fe(III) porphyrin and 714 (3 mmol, Aldrich) of lidocaine were dissolved in a 1:2 acetonitrile:pH7 phosphate buffer. To this solution was added 1.7 g (8 mmol) of iodosobenzene, and the reaction was stirred for 4 hr at room temperature. The solution was extracted with 3×5 ml of methylene chloride. The organic extract was dried over $MgSO_4$ and evaporated under reduced pressure. The residue was chromatographed over neutral alumina, eluting with 1:1 methylene chloride:hexane. Six metabolites were obtained (see Scheme 5): ω-(ethylamino)-2,6-dimethylacetanilide (L-1) 34%, ω-amino-2,6-dimethylacetanilide (L-2) 6%, ω-diethylamino-2-hydroxymethyl-6-methylacetanilide (L-3) 4%, and lidocaine N-oxide (L-4) 15%, and small amounts of cyclic metabolites, 1-ethyl-2methyl-3-(2,6-dimethylphenyl)-imidazolin-4-one (L-8) 2%, and 2-methyl-3-(2,6dimethylphenyl)-imidazolin-4-one (L-9) 3%.

EXAMPLE 8

Oxidation of Lidocaine in Organic Solvents

Iodosobenzene (0.3 mmol) was progressively added over 30 min at 0° C. to a 2 ml solution of lidocaine HCl (0.15 mmol) and of octachloro-octachloro tetrasulfonato Fe(III) porphyrin (0.5 μmol) in 1:20 methanol:acetonitrile. After 5 hr, the solution was evaporated at 20° C. under reduced pressure. The residue was chromatographed over neutral alumina, eluting with benzene. Compound L-1 and L-2 were obtained as major products and L-8 as a minor product; compounds which had not previously been reported to be metabolites of lidocaine include 3-hydroxy-ω-diethylamino-2,6-dimethylacetanilide (L-5) 13%, and 4-hydroxy-ω-diethylamino-2,6-dimethylacetanilide (L-6) 2%, 2hydroxymethyl-ω-diethylamino-2,6-dimethylacetanilide (L-7) 2%, as well as a small amounts of L-4 and L-9 (all known compounds).

EXAMPLE 9

Oxidation of 2,6-dimethylaniline

Example 8 above was repeated, substituting 2,6-dimethylaniline (L-7, see Scheme 6) for the lidocaine thereof. Oxidation products which were isolated are: 2,6-dimethylphenylhydroxylamine (L-7) 12%, 4-hydroxy-2,6-dimethylaniline (L-8) 5%, and 2,6-dimethylbenzoquinone (L-9) 2%.

EXAMPLE 10

Preparation of Octachloro-Octabromoporphyrinato-Iron(III)

10a. Octachloroporphyrinato-zinc(II)

2,6-Dichlorobenzaldehyde (100 g, 0.57 mol), anhydrous zinc acetate (30 g), and 2,6-lutidine (300 mL) were heated in a 1 L 3-neck flask fitted with a reflux condenser and a drying tube. When the temperature reached 100° C., pyrrole (40 mL, 0.57 mol) was added dropwise within 10 min, and the reaction mixture was refluxed for 16 hr. The solvent was removed under vacuum, and the residue was triturated with toluene (400 mL). Methanol (100 mL) was added and the mixture was held at 5° C. for 16 hr. The precipitate was collected by filtration and dissolved in 500 mL of chlorform, to which was then added 50 mL of trifluoroacetic acid. The mixture was stirred at room temperature for 16 hr under nitrogen. Water (250 mL) was added, and the mixture was stirred vigorously for 10 min. The organic phase was washed with satd $NaHCO_3$ and water, dried over $Na_2SO_4$. Ten g of p-chloranil was added, and the mixture was refluxed for 2 hr under $N_2$. The mixture was held at room temperature for 16 hr, reheated to reflux, and clarified by passage through a column of alumina. The solution was concentrated to a 200 mL volume, and 200 mL of methanol was added. The chloroform was removed from the solvent under vacuum, and the resulting suspension was filtered. The porphyrin (27 g) was dissolved in 500 mL of DMF, solid zinc acetate was added, and the mixture was refluxed for 30 min. The resulting precipitate was collected, washed with water and methanol, then dried to give 7.26 g of the title compound as a purple solid. UV/vis absorption ($CH_2Cl_2$), nm (relative intensity): 627.0 (0.91), 584.5 (1.71, (550.0 (12.08), 513.0 (1.82), 486.5 (1.49), 420.0 (100.0), 399.0 (23.1). MS m/z:1585 $(M+H)^+$.

10b. Alternate, large-scale preparation of octachloroporphyrinato-zinc(II)

2,6-Dichlorobenzaldehyde (750 g, 4.29 mol), anhydrous zinc acetate (580 g), and 2,6-lutidine (5.0 L) were heated in a 12 L 4-neck flask fitted with a reflux condenser and a drying tube. When the temperature reached 90°–100° C., pyrrole (600 mL, 4.29 mol) was added slowly within 10 min, and the reaction mixture was refluxed for 18 hr. The solvent was removed under vacuum, and the residue was triturated with toluene (6 L). Methanol (500 mL) was added and the mixture was held at 5° C. for 16 hr. The precipitate was collected by filtration, rinsed with methanol, and dried under vacuum. The dried compound was suspended in 6.0 L of hot chloroform and 6.0 L of methanol was added. The solvent was slowly evaporated under vacuum to remove the chloroform, and the resulting purple precipitate was collected by filtration, rinsed with methanol, water and pentane, and dried under vacuum to give 357 g of the title compound. A 30 g sample of this crude product was dissolved in 1.5 L of chloroform and 150 mL of Trifluoroacetic acid was added slowly. The mixture was stirred at room temperature for 16 hr under $N_2$. Water (1.5 L) was added, and the mixture was stirred vigorously for 10 min. The organic phase was washed with satd $NaHCO_3$ and water, dried over $Na_2SO_4$, transferred to a round-bottom flask, then 30 g of p-chloranil was added and the mixture was refluxed for 3 hr under $N_2$. The hot solution was passed through a column of alumina, which was rinsed with hot chloroform. The solution was concentrated to a 200 mL volume, and 200 mL of methanol was added. The chloroform was removed from the under vacuum, and the resulting suspension was filtered, to yield 7.98 g of the porphyrin. The porphyrin was dissolved in 750 mL of DMF, solid zinc acetate (20 g) was added, and the mixture was refluxed for 2 hr. The solution was cooled, 550 mL of DMF was distilled off under vacuum, and 200 mL of water was added. The resulting precipitate was collected, washed with water and methanol, then dried to give 9.13 g of the title compound as a purple solid.

10c. Octachloro-octabromoporphyrinato-zinc(II)

A 0.5 g (0.525 mmol) sample of the octachloro zinc porphyrin compound (from step 11a or 11b above) was dissolved in 50 mL of methanol and treated with bromine (0.27 mL, 5.25 mmol). The resulting mixture was heated at reflux for 1 hr. The mixture was taken to dryness, and the residue was chromatographed on alumina (neutral, Brockmann type 1), eluting with $CHCl_3$. The dark green band was collected and the solvent was removed under vacuum to afford the title compound as a green solid (0.332 g, 39% yield). UV/vis absorption ($CH_2Cl_2$), nm (relative intensity): 594 (7.49), 462 (100), 371 (14.15).

10d. Octachloro-octabromoporphyrinato-iron(III)

The compound from the step 11c was converted into the hemin metalloporphyrin by the method of Kobayashi et al. (*Bull. Chem. Soc. Japan*, 48:3137 (1975)).

EXAMPLE 11

Alternate Preparation of Octachloro-Octabromoporphyrinato-Iron(III)

11a. Octachloro-octabromoporphyrinato-zinc(II)

A sample of meso-tetrakis-(2,6-dichlorophenyl) porphyrinato-zinc(II) (0.5 g, 0.525 mmol, from steps 10a or 10b) was dissolved in 50 mL of methanol and treated with bromine (0.27 mL, 5.25 mmol). The resulting mixture was stirred at room temperature for 1.5 hr, and held at 4° C. for 16 hr. The precipitate was collected by filtration and washed with a small amount of methanol to give 0.268 g (65% yield) of the title product. UV-vis absorption ($CH_2Cl_2$), nm (relative intensity): 594 (7.0), 463 (100), 368.5 (11.5). MS M/Z $(m+H)^+$: 1585.

11b. Octachloro-octabromoporphyrinato-iron(III)

The compound from the step 11a was converted into the hemin metalloporphyrin by the method of Kobayashi et al. (*Bull. Chem. Soc. Japan*, 48:3137 (1975)).

EXAMPLE 12

Preparation of Octachloro-Octachloroporphyrinato-Iron(III)

12a. Octachloro-octachloroporphyrinato-zinc(II)

A sample of meso-tetrakis-(2,6-dichlorophenyl) porphyrinato-zinc(II) (0.250 g, 0.262 mmol, from steps 10a or 10b) was suspended in 50 mL of methanol, and the mixture was cooled to 0° C. with an ice bath. Chlorine gas was bubbled into the mixture at a rate such that the temperature remained below 5° C. After 15–20 minutes, the color of the reaction mixture changed from purple to green, and starting material was no longer present. The solvent and unreacted chlorine was removed under vacuum to give a purple solid (0.283 g 88% yield). UV-vis absorption ($CH_2Cl_2$), nm (relative intensity): 436.0 (100), 485.0 (50), 523.0 (9.5), 575.0 (9.5), 625.0 (9.3). MS M/Z (relative intensity): 1338 (25), 1305 (45), 1266 (50), 1230 (100), 1195 (60), 1160 (55).

12b. Octachloro-octachloroporphyrinato-iron(III)

The compound from the step 12a was converted into the hemin metalloporphyrin by the method of Kobayashi et al. (*Bull. Chem. Soc. Japan*, 48:3137 (1975)).

EXAMPLE 13

Oxidation of ABT-418 in Organic Solvent

ABT-418 (0.506 mg) was dissolved in 10 mL of methylene chloride, and 8 mg octachloro-octabromo Fe(III) porphyrin (0.5 µmol) was added. The mixture was stirred vigorously, and 0.511 mg of iosdosobenzene was added in small portions. After 5 hr, the solution was evaporated at 20° C. under reduced pressure, and the residue was redissolved in 10 mL of methylene chloride. The solution was analyzed by HPLC, and the products were identified by comparison with known samples of metabolites (cf., Sullivan et al., mss in preparation).

EXAMPLE 14

Oxidation of ABT-418 in Aqueous System

ABT-418 (0.498 g ) was dissolved in 10 mL of 4:1 acetonitrile:water solution. To this was added 8 mg of octachloro-octabromo-tetrasulfonate Fe(III) porphyrin, followed by 2 mL of aqueous sodium hypochlorite. The reaction was stirred for 8 hr, and the layers were separated. The layers were examined by HPLC, and the products were identified by comparison with known samples of metabolites.

EXAMPLE 15

Oxidation of Odapipam

Odapipam (10 µmol) was dissolved in 1 mL of methylene chloride, and 1 µmol of pentafluoroFe(III) porphyrin and 40 µmol of iodosobenzene were added. After reaction was complete, the products were separated by HPLC and identified by mass spectroscopy (cf O'Boyle et al., *Pharmac. Therap.*, 43:1, (1989)).

EXAMPLE 16

Systematic Oxidation of Aminopyrine

Twenty-seven flasks, each containing 50 mg of aminopyrine are prepared, and solvents, synthetic metalloporphyrins and oxidizing reagents are added to the flasks according to Table 4a–4c below (see abbreviations below). The contents are mixed for 4 hr at room temperature, and the solvents are removed under vacuum. The residues are taken up in methylene chloride, and the products are identified by HPLC, mass spectroscopy, NMR spectroscopy and elemental analysis.

Abbreviations used in Tables 4a–4c below: A= methylene chloride; B= 20% (v/v) acetonitrile in water; C= pH 6 phosphate buffer; D= octachloro-octabromo Fe(III) porphyrin; E= octachloro-octabromo MN(II) porphyrin; F= octachloro-octachloro tetrasulfonato Fe(III) porphyrin; G= octachloro-octachloro tetrasulfonato Mn(II) porphyrin; H= iodosobenzene; I= sodium hypochlorite; J= tert-butyl hydroperoxide; and K= potassium monopersulfate.

TABLE 4a

Combination of solvent, smp and oxidizing reagents in flasks 1–16.

| Fl | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| S | A | A | A | A | A | A | A | A | A | A | A | A | A | A | A | A |
| smp | D | D | D | D | E | E | E | E | F | F | F | F | G | G | G | G |
| ox | H | I | J | K | H | I | J | K | H | I | J | K | H | I | J | K |

Fl = flask; S = solvent; smp = synthetic metalloporphyrin; ox = SMP-co-oxidizing reagents

TABLE 4b

Combination of solvent, smp and oxidizing reagents in flasks 17–32.

| Fl  | 17 | 18 | 19 | 20 | 21 | 22 | 23 | 24 | 25 | 26 | 27 | 28 | 29 | 30 | 31 | 32 |
|-----|----|----|----|----|----|----|----|----|----|----|----|----|----|----|----|----|
| S   | B  | B  | B  | B  | B  | B  | B  | B  | B  | B  | B  | B  | B  | B  | B  | B  |
| smp | D  | D  | D  | D  | E  | E  | E  | E  | F  | F  | F  | F  | G  | G  | G  | G  |
| ox  | H  | I  | J  | K  | H  | I  | J  | K  | H  | I  | J  | K  | H  | I  | J  | K  |

Fl = flask; S = solvent; smp = synthetic metalloporphyrin; ox = SMP-co-oxidizing reagents

TABLE 4c

Combination of solvent, smp and oxidizing reagents in flasks 33–48.

| Fl  | 33 | 34 | 35 | 36 | 37 | 38 | 39 | 40 | 41 | 42 | 43 | 44 | 45 | 46 | 47 | 48 |
|-----|----|----|----|----|----|----|----|----|----|----|----|----|----|----|----|----|
| S   | C  | C  | C  | C  | C  | C  | C  | C  | C  | C  | C  | C  | C  | C  | C  | C  |
| smp | D  | D  | D  | D  | E  | E  | E  | E  | F  | F  | F  | F  | G  | G  | G  | G  |
| ox  | H  | I  | J  | K  | H  | I  | J  | K  | H  | I  | J  | K  | H  | I  | J  | K  |

Fl = flask; S = solvent; smp = synthetic metalloporphyrin; ox = SMP-co-oxidizing reagents

What is claimed is:

1. A process for the systematic preparation of oxidative products of a drug candidate compound, comprising reacting samples of the drug candidate compound with a series of combinations of a synthetic metalloporphyrin (SMP), an oxidizing agent (OA) and a solvent, for a period of up to 24 hours, at temperature from 0° C. to the reflux temperature of the solvent, wherein each sample of drug candidate compound is reacted with a different combination of said SMP, OA, and solvent, wherein at least two samples contain a different SMP, at least two samples contain a different OA and at least two samples contain a different solvent, followed by separating and isolating the resulting oxidative products, and wherein said SMP is of the formula

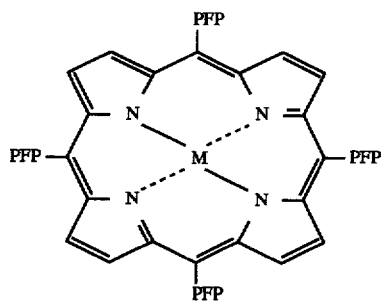

(1)

or

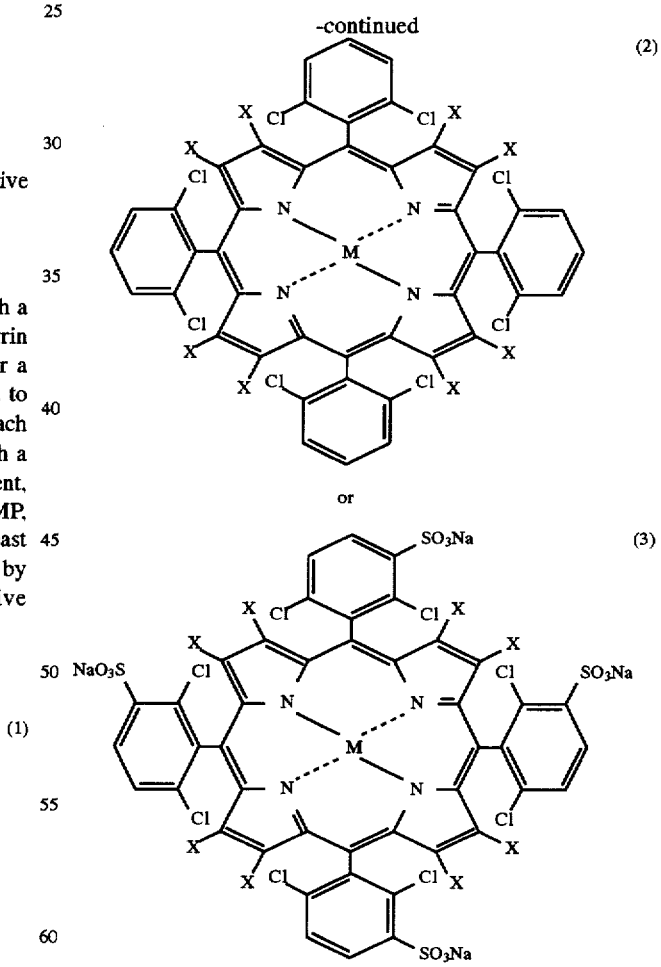

wherein PFP represents perfluorophenyl,
M is an ion of iron, manganese, chromium, ruthenium, cobalt, copper or nickel,
X is Cl, Br, $NO_2$, CN or sulfonate and wherein each Cl in formulas (2) and (3) may be independently replaced by $NO_2$, CN or sulfonate and wherein each sulfonate in formula (2) or (3) may be independently replaced by carboxyl.

2. The process according to claim 1, wherein each SMP is selected from the group consisting of octachloro-octabromo Fe(III) porphyrin, octachloro-octabromo Mn(II) porphyrin, octachloro-octachloro Fe(III) porphyrin, octachloro-octachloro Mn(II) porphyrin, octachloro-octabromo tetrasulfonato Fe(III) porphyrin, octachloro-octabromo tetrasulfonato Mn(II) porphyrin, octachloro-octachloro tetrasulfonato Fe(III) porphyrin, octachloro-octachloro tetrasulfonato Mn(II) porphyrin, octachloro-tetranitro Fe(III) porphyrin, octachloro-tetranitro Mn(II) porphyrin, octachloro-octacyano Fe(III) porphyrin, and octachloro-octacyano Mn(II) porphyrin.

3. The process according to claim 1, wherein the OA is selected from the group consisting of iodosobenzene, sodium hypochlorite, potassium monopersulfate, ozone, hydrogen peroxide, m-chloroperbenzoic acid, cumene hydroperoxide and tert-butyl hydroperoxide.

4. The process according to claim 1, wherein the solvent is selected from the group consisting of $CH_2Cl_2$, $CH_3CN$, 20% methanol in $H_2O$, 20% $CH_3CN$ in $H_2O$, and buffered aqueous solutions thereof.

5. The process according to claim 1, wherein the SMP is selected from the group consisting of octachloro-octabromo Fe(III) porphyrin, octachloro-octabromo Mn(II) porphyrin, octachloro-octachloro tetrasulfonato Fe(III) porphyrin, and octachloro-octachloro tetrasulfonato Mn(II) porphyrin; the OA is selected from the group consisting of iodosobenzene, sodium hypochlorite, tert-butyl hydroperoxide, and potassium monopersulfate; and the selected from the group consisting of $CH_2Cl_2$, 20% $CH_3CN$ in $H_2O$, and buffered aqueous solutions thereof.

6. A method for systematic preparation of oxidative products of a drug candidate compound which method comprises reacting samples of the drug candidate compound with a series of combinations of a synthetic metalloporphyrin (SMP) an oxidizing agent (OA) and a solvent for a period of up to 24 hours at a temperature of from 0° C. to the reflux temperature of the solvent wherein in each sample, the SMP is selected from a set of at least two different SMPs, the OA is selected from a set of at least two different OAs and the solvent is selected from a set of at least two different solvents, and wherein each possible combination of SMP, OA and solvent is reacted with a sample of said drug candidate compound followed by separating and isolating the resultant oxidative product.

7. A method for systematic preparation of oxidative products of a drug candidate compound which method comprises reacting samples of the drug candidate compound with a series of combinations of a synthetic metalloporphyrin (SMP) an oxidizing agent (OA) and a solvent for a period of up to 24 hours at a temperature of from 0° C. to the reflux temperature of the solvent wherein in each sample, the SMP is selected from a set of at least two different SMPs, the OA is selected from a set of at least two different OAs and the solvent is selected from a set of at least two different solvents, and wherein each SMP and each OA and each solvent is represented in said combinations followed by separating and isolating the resultant oxidative product, and wherein said SMP is of the formula

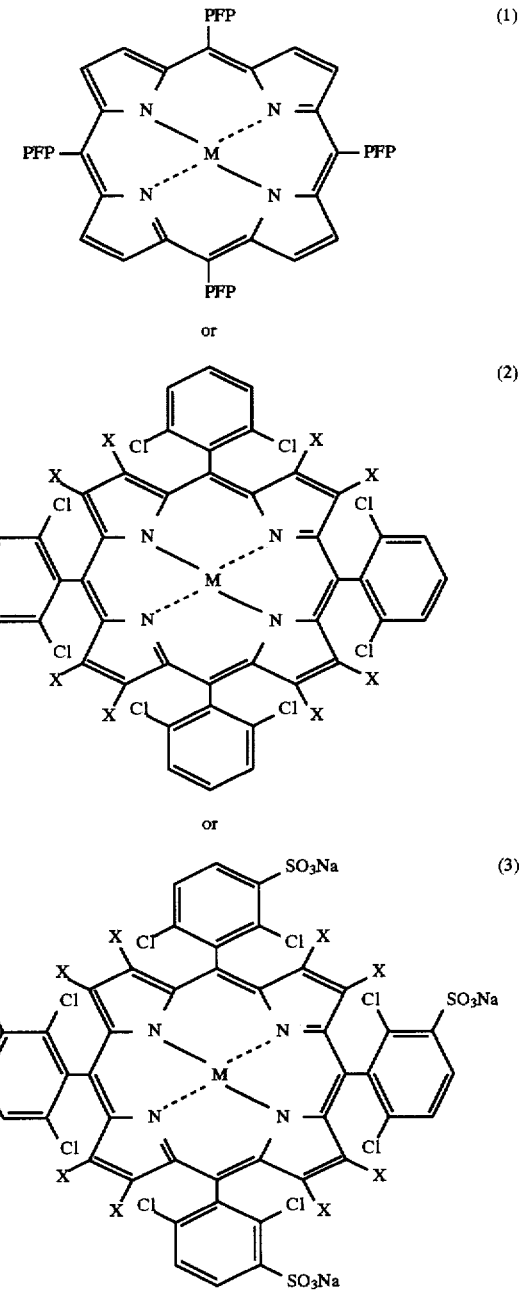

wherein PFP represents perfluorophenyl,

M is an ion of iron, manganese, chromium, ruthenium, cobalt, copper or nickel,

X is Cl, Br, $NO_2$, CN or sulfonate and wherein each Cl in formulas (2) or (3) may be independently replaced by $NO_2$, CN or sulfonate and wherein each sulfonate in formula (2) or (3) may be independently replaced by carboxyl.

* * * * *